(12) United States Patent
Schwartz

(10) Patent No.: US 10,412,785 B1
(45) Date of Patent: Sep. 10, 2019

(54) MANUALLY ACTIVATED VAPORIZING OR SMOKING DEVICE

(71) Applicant: YETS Innovations, Inc., Chicago, IL (US)

(72) Inventor: Yitzchok Moshe Schwartz, Chicago, IL (US)

(73) Assignee: YETS Innovation, Inc., Chicago, IL (US)

( * ) Notice: Subject to any disclaimer, the term of this patent is extended or adjusted under 35 U.S.C. 154(b) by 179 days.

(21) Appl. No.: 15/702,468

(22) Filed: Sep. 12, 2017

Related U.S. Application Data

(63) Continuation-in-part of application No. 14/996,739, filed on Jan. 15, 2016, now Pat. No. 10,098,385.

(60) Provisional application No. 62/125,277, filed on Jan. 16, 2015.

(51) Int. Cl.
| | |
|---|---|
| *H05B 3/16* | (2006.01) |
| *H05B 3/06* | (2006.01) |
| *A24F 47/00* | (2006.01) |

(52) U.S. Cl.
CPC .............. *H05B 3/16* (2013.01); *H05B 3/06* (2013.01); *A24F 47/008* (2013.01); *A61M 2205/8206* (2013.01); *H05B 2203/014* (2013.01); *H05B 2203/021* (2013.01)

(58) Field of Classification Search
CPC .... A24F 47/008; A24F 47/002; A24F 47/004; A24F 47/006; A61M 15/0021; A61M 2205/8206; A61M 15/06; A61M 15/002; H05B 3/16; H05B 3/06; H05B 2203/021; H05B 2203/014
See application file for complete search history.

(56) References Cited

U.S. PATENT DOCUMENTS

| | | |
|---|---|---|
| D653,803 S | 2/2012 | Timmermans |
| D684,311 S | 6/2013 | Liu |
| 8,550,069 B2 | 10/2013 | Alelov |
| (Continued) | | |

FOREIGN PATENT DOCUMENTS

| | | |
|---|---|---|
| CN | 203378558 U | 1/2014 |
| WO | 2015184747 A1 | 12/2015 |

OTHER PUBLICATIONS

YOCAN Products Inc. web pages printed on Jan. 15, 2016.
Abstract of CN 203378558.

*Primary Examiner* — Joseph S Del Sole
*Assistant Examiner* — Mohamed K Ahmed Ali
(74) *Attorney, Agent, or Firm* — Brian Roffe

(57) ABSTRACT

Smoking device includes a housing defining two chambers, and a heating system that heats material in the chambers when in contact with part of the heating system. An activation system activates the heating system. An outlet portion includes a mouthpiece and an adapter configured to fit over the mouthpiece. The outlet portion also includes an upper cap having a first conduit leading from an area above one chamber, a second conduit leading from an area above the other chamber, and a single outflow conduit communicating with both chambers and in flow communication with the mouthpiece. A plunger system presses material in each chamber against the part of the heating system and includes a spring retained at one end on the housing and a board attached at an opposite end of the spring and that is urged by the spring toward the heated part of the heating system.

21 Claims, 12 Drawing Sheets

(56) References Cited

U.S. PATENT DOCUMENTS

| | | |
|---|---|---|
| 8,733,345 B2 | 5/2014 | Siller |
| 8,794,231 B2 | 8/2014 | Thorens et al. |
| D720,499 S | 12/2014 | Alima |
| D720,881 S | 1/2015 | Liu |
| D723,216 S | 2/2015 | Chen |
| D724,264 S | 3/2015 | Chambers |
| D727,562 S | 4/2015 | Li |
| D727,566 S | 4/2015 | Xiao |
| D748,852 S | 2/2016 | Wu |
| D751,249 S | 3/2016 | Chen |
| D752,278 S | 3/2016 | Verleur |
| 9,271,528 B2 | 3/2016 | Liu |
| D758,649 S | 6/2016 | Liu |
| D758,654 S | 6/2016 | Liu |
| D759,303 S | 6/2016 | Afridi |
| D760,948 S | 7/2016 | Eksourian |
| D764,703 S | 8/2016 | Liu |
| D767,819 S | 9/2016 | Kayvon |
| D767,822 S | 9/2016 | Jordan |
| 9,451,793 B2 | 9/2016 | Zhou |
| D768,914 S | 10/2016 | Liu |
| D771,307 S | 11/2016 | Wu |
| D773,727 S | 12/2016 | Eksourian |
| D774,247 S | 12/2016 | Chen |
| D776,868 S | 1/2017 | Rado |
| 9,591,876 B2 | 3/2017 | Alima |
| 9,675,108 B2 | 6/2017 | Liu |
| 9,687,029 B2 | 6/2017 | Liu |
| D822,272 S | 7/2018 | Miller et al. |
| D822,894 S | 7/2018 | Schwartz et al. |
| D827,921 S | 9/2018 | Miller et al. |
| D831,269 S | 10/2018 | Qiu |
| 10,098,385 B1 | 10/2018 | Schwartz |
| 10,123,568 B1 | 11/2018 | Zhu |
| 2011/0094524 A1 | 4/2011 | Glover |
| 2012/0255546 A1 | 10/2012 | Goetz et al. |
| 2013/0087160 A1 | 4/2013 | Gherghe |
| 2013/0152922 A1 | 6/2013 | Bennasayag et al. |
| 2013/0192615 A1 | 8/2013 | Tucker et al. |
| 2013/0319407 A1 | 12/2013 | Liu |
| 2014/0041655 A1 | 2/2014 | Barron et al. |
| 2014/0246035 A1 | 9/2014 | Minskoff et al. |
| 2015/0090253 A1 | 4/2015 | Farrow |
| 2015/0237914 A1 | 8/2015 | Han |
| 2015/0342258 A1 | 12/2015 | Chen |
| 2015/0351455 A1 | 12/2015 | Liu |
| 2016/0198771 A1 | 7/2016 | Goggin et al. |
| 2016/0331026 A1 | 11/2016 | Cameron |
| 2016/0353800 A1 | 12/2016 | Di Carlo |
| 2017/0095004 A1* | 4/2017 | Liu .................. A24F 47/008 |

\* cited by examiner

MANUALLY ACTIVATED VAPORIZING OR SMOKING DEVICE

CROSS REFERENCE TO RELATED APPLICATIONS

This application is a continuation-in-part of U.S. patent application Ser. No. 14/996,739, filed Jan. 15, 2016, now U.S. Pat. No. 10,098,385, which claims priority of U.S. provisional patent application Ser. No. 62/125,277 filed Jan. 16, 2015, now expired, both of which are incorporated by reference herein.

FIELD OF THE INVENTION

The present invention relates to a mechanical vaporizing or smoking device.

BACKGROUND OF THE INVENTION

Various portable smoking apparatus are known in the art. For example, U.S. Pat. Appln. Publ. No. 2011/0094524 (Glover) describes a smoking apparatus for vaporizing smoking products such as tobacco and herb products. The smoking apparatus is preferably made entirely out of glass and comprises a bowl at a first end that receives the smoking product through an open top end, a screen support area immediately below the bowl having one or more screen supports, a product support pellet that rests on the screen supports to support the smoking product, a hollow stem in fluid flow communication with the bowl to allow the user to draw vapor from the bowl and a diffuser removably received in the open top end of the bowl for diffusing heat across the smoking product to vaporize it. The diffuser has a diffusing element made out of the frit. It is alleged that no metal contacts the product, vapor or user. The smoking apparatus can be a pipe or an adapter for a water pipe.

U.S. Pat. Appln. Publ. No. 2012/0255546 (Goetz et al.) describes a portable vaporizer including a main body, a heating assembly coupled to the main body, a removable basket in thermal communication with the heating assembly and that allows an herb placed in the removable basket to be vaporized by the heating assembly, and an agitator device that agitates the herb placed in the removable basket to purportedly achieve a more uniform vaporization of the herb. A mouthpiece is removably attached to the main body in air flow communication with the heating assembly. An opening of the main body receives and stores the mouthpiece when the mouthpiece is not in use.

U.S. Pat. Appln. Publ. No. 2013/0152922 (Benassayag et al.) describes a portable pen-sized electric herb vaporizer with ceramic heating chamber. The vaporizer is used to vaporize active ingredient of or burn herbs, and includes a battery, a heating compartment, a chamber connector, and a mouthpiece. Two threaded screw interfaces attach the battery to the heating compartment and the heating compartment to the chamber connector. The mouthpiece holds a ceramic filter and is inserted into the chamber connector. The heating compartment has a ceramic heating chamber within which herbs are placed, and a heating coil connected to the battery within the ceramic heating chamber heats the herbs. For use, the user presses an activator button and inhales through the mouthpiece, drawing heated air over the herbs, through the chamber connector and into the user's lungs. The chamber connector has a disk filter to catch ash and a spring that presses on the herbs for efficient vaporization.

U.S. Pat. Appln. Publ. No. 2014/0041655 (Barron et al.) describes a portable vaporizer including a power module having a battery tube, a cylindrical battery within the battery tube, a control housing, connected to the battery tube, and a control board inside the control housing. When the control housing is connected to the battery tube, the control board is electrically coupled to the cylindrical battery. A vaporization chamber is connectable to the power module and includes a vaporization tank having a tube, a tank base connected to the tube, a vaporization basket inside the tube and adapted to hold vaporization materials, a heating element inside the tube, and a cylindrical space between the vaporization basket and the tube. A mouthpiece is connectable to the vaporization chamber and includes a passageway leading from the vaporization chamber to the exterior of the portable vaporizer. When the heating element is activated, the air in the cylindrical space between the basket and the tube is heated and causes the vaporization materials in the vaporization basket to vaporize.

OBJECTS AND SUMMARY OF THE INVENTION

It is an object of the present invention to provide a new and improved smoking device.

In order to achieve this object and others, a first embodiment of a smoking device in accordance with the invention includes a housing defining at least one battery compartment each adapted to receive at least one battery, and at least one material chamber each adapted to receive inhalable material, and a selectively activated heating system that heats material in each chamber when the material is in contact with part of the heating system. The heating system includes a respective conductive electrode having a portion extending into the battery compartment and adapted to be contacted by a battery when present in the battery compartment. The smoking device also includes a manual activation system that activates the heating system, and an outlet portion including a mouthpiece having an interior in flow communication with each material chamber and an adapter configured to fit over the mouthpiece.

The outlet portion has a first configuration when the adapter is not over the mouthpiece and a second configuration when the adapter is over the mouthpiece and provides an outer circumference for the outlet portion that is larger than the outer circumference provided when the adapter is not over the mouthpiece. A user can place their mouth over the mouthpiece and directly inhale material being heated in each material chamber when the outlet portion is in the first configuration or connect an inlet of a water pipe or bong to the adapter when the adapter is fit over the mouthpiece when the outlet portion is in the second configuration.

The adapter may be a gasket or cone that defines an interior axial channel configured to removably receive the mouthpiece. An exterior surface of the cone may define two different diameter sections, a smaller diameter section having a diameter of about 14 mm and a second diameter section having a diameter of about 18 mm. These diameters are selected based on, for example, the inlet size of commercial water pipes or bongs. Other criteria for the selection of the size of the different diameter sections of the adapter may also be used.

The mouthpiece may include a tubular portion having a disc with perforations at an end closer to the material chamber(s) and an opening at an opposite end. The mouthpiece also has an engagement structure that removably engages the mouthpiece to the housing.

The housing includes at least one tube, a respective closure element that removably engages with a lower end of each tube to selectively close the lower end of the tube, and a respective spring attached to the closure element. The battery compartment is defined in the respective tube, and the respective spring is configured to urge a battery when present in the battery compartment upward against the respective electrode. For ventilating each battery compartment, each tube preferably includes at least one aperture extending through a side wall to the battery compartment and the closure element preferably includes an aperture extending therethrough to the battery compartment.

Additionally or alternatively, the housing includes a intermediate ring section, with the heating system and the manual activation system each being partly housed in or supported by the intermediate ring section.

The heating system may include a set of components for each material chamber, each set of components including a coil assembly each including a coil housing, an electrically activated coil arranged on the coil housing and a conductor element extending below the coil housing and connected to the coil, and a contact cylinder surrounding a portion of a respective one of the electrodes and electrically insulated therefrom by an insulating ring. The contact cylinder engages with the coil housing and is arranged in the intermediate ring section. An electrode contacts the respective conductor element of the coil assembly.

The manual activation system may include a spring housing extending through an opening in a side wall of the intermediate ring section, a conductive press button, a conductive actuating rod configured to be moved by movement of the press button into an interior of the intermediate ring section, and a spring that biases the press button to a position in which the manual activation system is not activating the heating system. The actuating rod is configured to contact one of the contact cylinders in the intermediate ring section when the press button is pushed or pressed inward to cause completion of an electrical circuit that provides electrical power to the heating system from a battery when present in each battery compartment and the coil(s) to heat up. When multiple contact cylinders are present, they are conductively coupled together by, for example, a conductive connector.

For each material chamber, a support disc supports the coil in the coil housing, and ventilation apertures are preferably arranged in the support disc, the conductor element, the contact cylinder and the side wall of the intermediate ring section to enable heat generated by the coil to dissipate through the ventilation apertures.

A removable protective ring, when present, interposes a blocking element between the press button and the spring housing to prevent the press button from being pushed or pressed inward and thus inadvertent activation of the heating system.

When there is a single material chamber, the housing may also include a connection ring removably engaging with the intermediate ring section and including a tubular container that defines the chamber, and a retainer removably engaging with the connection ring on an opposite side from the intermediate ring section. The container may be made of ceramic. The retainer and mouthpiece may include cooperating attachment structure to enable removable attachment of the mouthpiece to the retainer. The retainer includes an opening into which the mouthpiece is inserted and which is in flow communication with the chamber, in which case, the mouthpiece preferably includes a disc having perforations at an end inserted into the retainer.

When there are two material chambers, the outlet portion includes an upper cap that includes a first conduit leading from an area above a first chamber, a second conduit leading from an area above a second chamber, and a single outflow conduit communicating with the first and second chambers and in flow communication with the mouthpiece. The upper cap replaces the retainer which connects the connection ring to the mouthpiece.

Another embodiment of a smoking device in accordance with the invention includes a housing defining at least one battery compartment each adapted to receive at least one battery, and at least one material chamber each adapted to receive inhalable material, and which includes an intermediate section with a hollow interior. A selectively activated heating system heats material in the chamber(s) when the material is in contact with part of the heating system. The heating system is partly housed in or supported by the intermediate section and includes a respective conductive electrode having a portion extending into each battery compartment and adapted to be contacted by a battery when present in the battery compartment, and a respective coil assembly including a coil housing, an electrically activated coil arranged on the coil housing and a conductor element extending below the coil housing and connected to the coil. The electrode and conductor element of the coil assembly are in contact with one another. The heating system also includes a contact cylinder each surrounding a portion of the respective electrode and electrically insulated therefrom by an insulating ring. The contact cylinder engages with the coil housing and is arranged in the interior of the intermediate section.

As in the embodiment described above, a manual activation system activates the heating system and is partly housed in or supported by the intermediate section. A mouthpiece has an interior in flow communication with each material chamber, and includes a tubular portion having a disc with perforations at an end closer to the material chamber(s) and an opening at an opposite end, and removably engages the mouthpiece to the housing.

An adapter removably fits over the mouthpiece and provides an outer circumference that is larger than an outer circumference provided when the adapter is not fit over the mouthpiece. As such, a user can place their mouth over the mouthpiece when the adapter is not fit over the mouthpiece and directly inhale material being heated in the material chamber(s) or connect an inlet of a water pipe or bong to the adapter when the adapter is fit over the mouthpiece.

The same variations described for the first embodiment are applicable to this embodiment as well.

BRIEF DESCRIPTION OF THE DRAWINGS

The following drawings are illustrative of embodiments of the system developed or adapted using the teachings of at least one of the inventions disclosed herein and are not meant to limit the scope of the invention as encompassed by the claims.

DETAILED DESCRIPTION OF THE INVENTION

Figure 1:
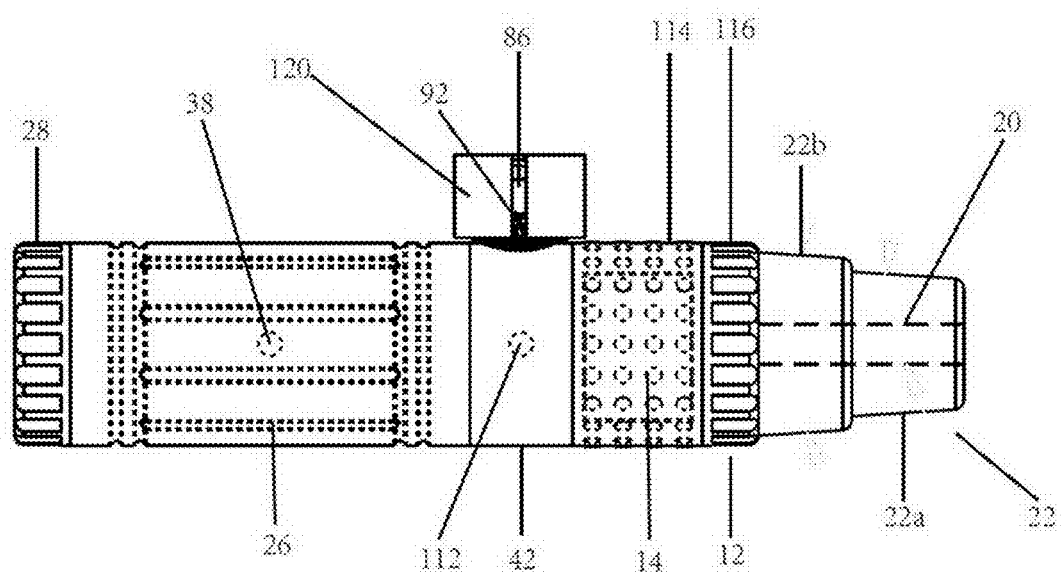
FIG. 1 is a side view of a mechanical smoking device in accordance with the invention showing an adapter in place.
Figure 2:
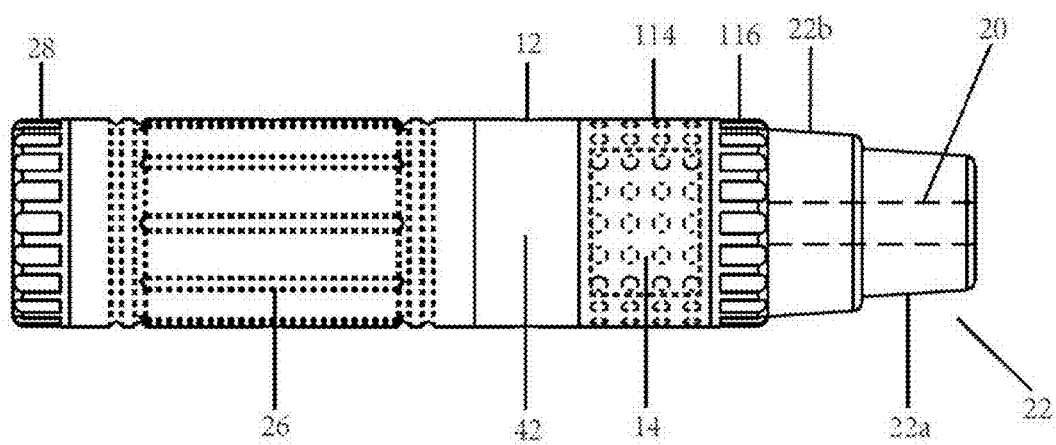
FIG. 2 is a rear view of the mechanical smoking device in accordance with the invention showing an adapter in place.
Figure 3:
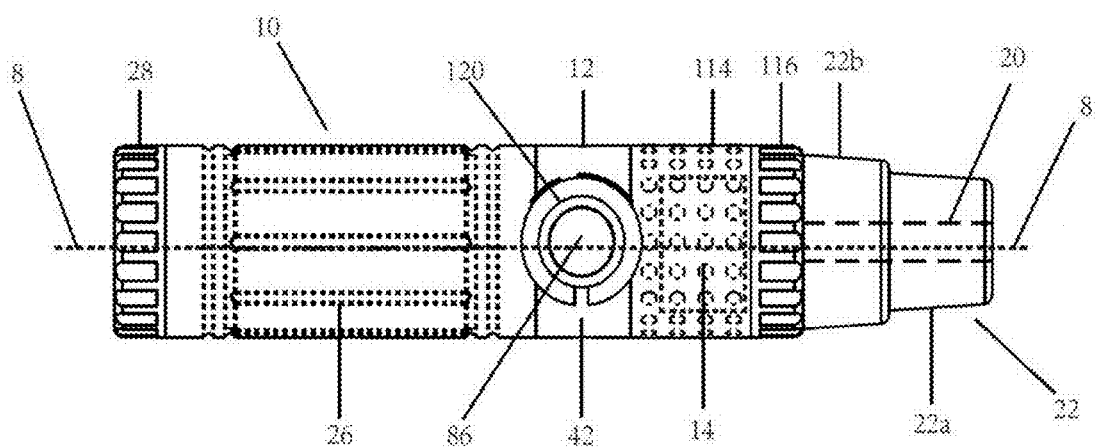
FIG. 3 is a front view of the mechanical smoking device in accordance with the invention showing an adapter in place.

Referring to the accompanying drawings wherein like reference numbers refer to the same or similar elements. FIG. 1 shows a smoking device 10 in accordance with the invention in its upright position. Generally, the smoking device 10 includes a housing 12 defining a chamber 14 into which a material sought to be heated and its vapor inhaled, e.g., dry herbs, may be placed to be "smoked", and a heating system 16 that is activated to heat the interior of the chamber 14. Thus, when dry herbs are present in the chamber 14, the heating system 16 would be activated to heat the dry herbs causing them to heat up and release gaseous vapors derived from the herbs. This release occurs, for example, as a user inhales through an outlet portion of the housing 12. Additionally, the smoking device 10 includes a manual activation system 18 that, when operated by a user, activates the heating system 16 causing it to heat the interior of the chamber 14, and thus dry herbs when present in the chamber 14.

Smoking device 10 is configured to provide two alternative delivery options for vapors generated from the heating of herbs, or other material, in the chamber 14. This is effected by providing an outlet portion of the housing 12 having two different configurations. A first option for the outlet portion involves the presence of an uncovered mouthpiece 20 in flow communication with the interior of the chamber 14, and which enables the smoking device to be used as a conventional pipe. The second option for the outlet portion involves the placement of an adapter or cone 22 over the mouthpiece 20 and which is configured to be received in the inlet of a bong or water pipe (not shown).

Figure 6:
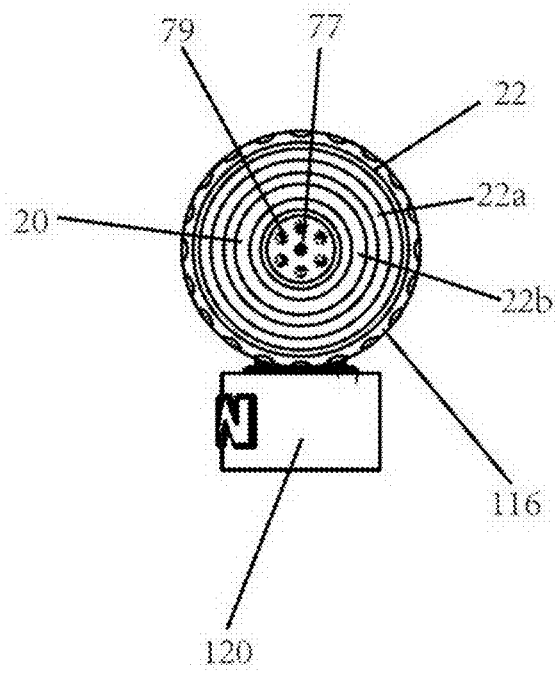
FIG. 6 is a top view of the mechanical smoking device in accordance with the invention.
Figure 7:
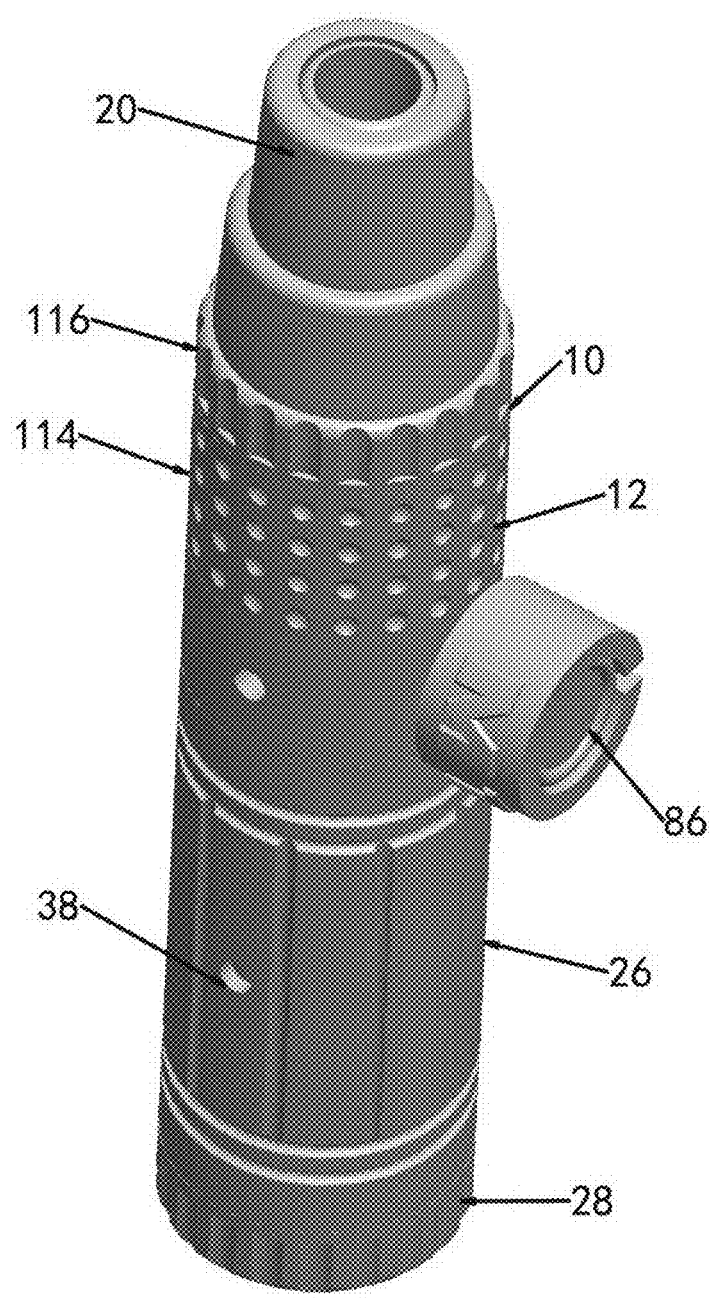
FIG. 7 is a perspective view of the mechanical smoking device in accordance with the invention showing the adapter removed and the mouthpiece exposed.

With respect to the first delivery option, mouthpiece 20 comprises a tubular portion having an opening at one end. The opposite end of the tubular portion has a disc 77 with perforations 79 (see FIG. 6). The interior of the mouthpiece 20 is in flow communication with the interior of the chamber 14. As such, when the user places their mouth over the uncovered mouthpiece 20 and inhales, they draw herb vapor-infused air from the chamber 14 through the perforations 79 and the mouthpiece 20 into their mouth.

Figure 8:
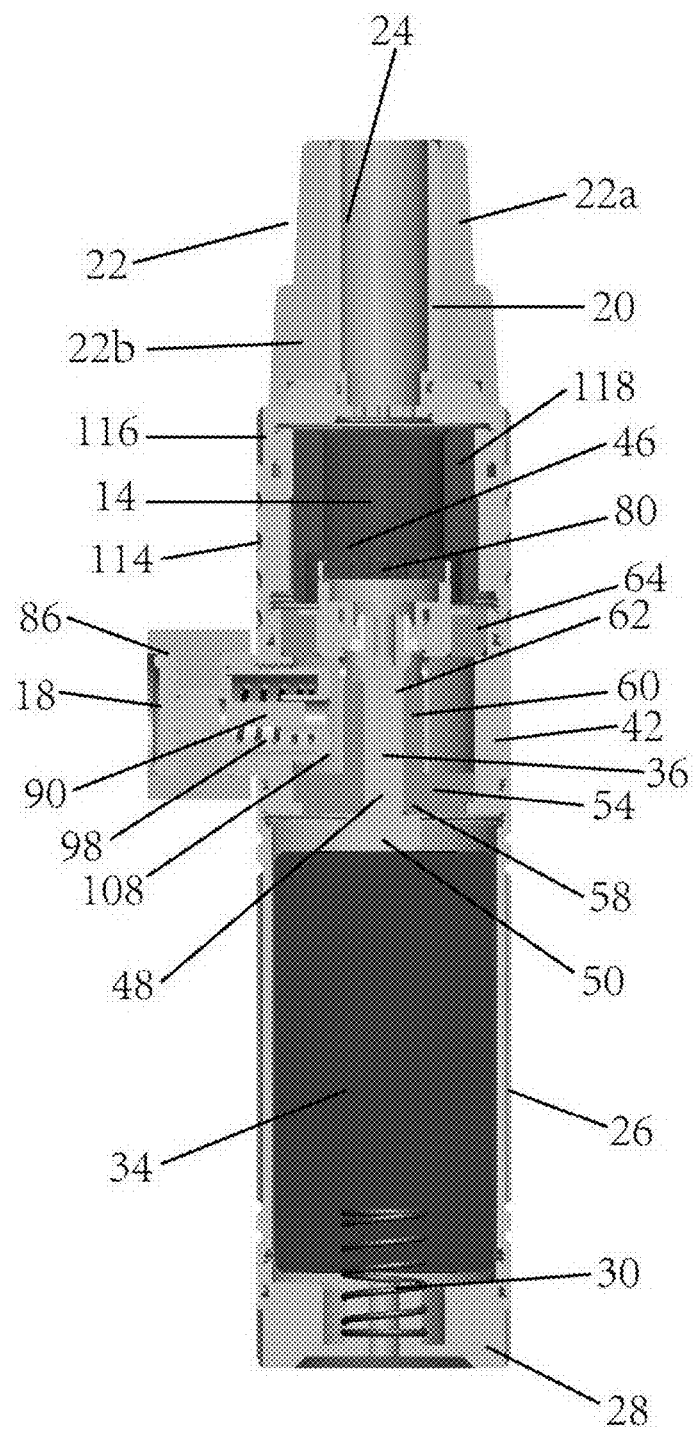
FIG. 8 is a cross-sectional view of the mechanical smoking device in accordance with the invention taken along the line 8-8 in FIG. 3.

The second delivery option involves the presence of the cone 22 over the mouthpiece 20 to enable the smoking device 10 to be coupled to a water pipe or bong, or other similar type of device (referring to generally herein as an inhaling appliance). To this end, the cone 22 defines an interior axial channel 24 which removably receives the mouthpiece 20 in a secure manner (see FIG. 8). The exterior surface of the cone 22 defines two different diameter sections, a first smaller diameter section 22a having a diameter of about 14 mm and a second, larger diameter section 22b having a diameter of about 18 mm. The cone 22 can thus be engaged with an inlet of a water pipe having a diameter of about 14 mm or about 18 mm, which are fairly standard diameters for inlets to water pipes. It is of course possible to provide different configurations and dimensions of the cone 22 to enable its engagement with different size inlets of water pipes. Also, the cone 22 may have a number of different sized diameter sections other than 2 as shown, and in all embodiments, each different sized section may be tapered if so desired.

Cone 22 may be made of silicone or rubber while the mouthpiece 20 may be made of copper. Cone 22 may be considered a gasket or protector.

When used for this delivery option, a suction force is generated in the water pipe which causes herb vapor-infused air to be drawn from the chamber 14 through the perforations 79 in the mouthpiece 20 and into and through the mouthpiece 20 into the inlet of the water pipe.

It is possible to switch between the different delivery options by either placing the cone 22 over the mouthpiece 20 or removing the cone 22 from engagement with the mouthpiece 20. Preferably, the interior axial channel 24 accommodates the mouthpiece 20 with a tight fit to prevent inadvertent separation of the cone 22 from the mouthpiece 20.

As to specifics of the housing 12, the housing 12 includes a lower section having a hollow interior and opposed open ends, which in the illustrated embodiment is a tube 26, and a bottom cap or closure element 28 that engages with a lower end of the tube 26 to selectively close this end of the tube 26. A spring 30 is attached to the closure element 28 (see FIG. 10). A battery compartment 32 is defined in the tube 26 and one or more batteries 34 can be securely retained in the battery compartment 32. In the illustrated embodiment, battery compartment 32 is configured to retain only a single battery. Battery 34 may be a lithium battery and the size of the tube 26 is preferably dimensioned relative to the size of the battery 34 to provide for a snug fit.

Insertion of the battery 34 into the battery compartment 32 is enabled by separating the closure element 28 from the tube 26 and then after insertion of the battery 34, re-engaging the closure element 28 with the tube 26. The engagement of the closure element 28 and the tube 26 may be a threaded engagement, e.g., threads are formed on an inner surface at the lower end of the tube 26 and corresponding threads on the outer surface of an upper rim of the closure element 28. The spring 30 urges the battery 34, when present in the battery compartment 32, upward against an electrode 36 that has a portion extending into the battery compartment 32. Electrode 36 is thus contacted by a terminal of the battery 34. Instead of direct contact between the battery 34 and the electrode 36, it is also possible to have a coupling through an intermediate structure that is electrically conductive.

Figure 4:
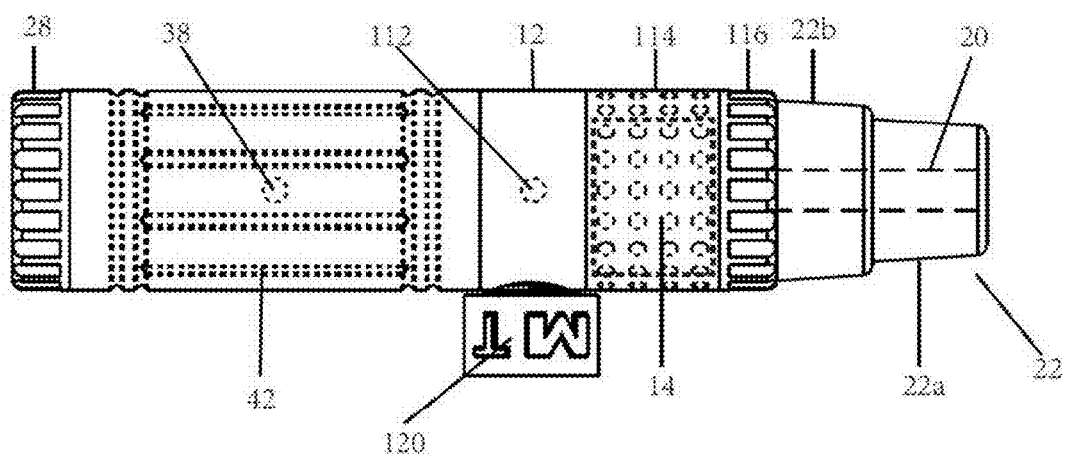
FIG. 4 is the other side view of the mechanical smoking device in accordance with the invention showing an adapter in place.
Figure 5:
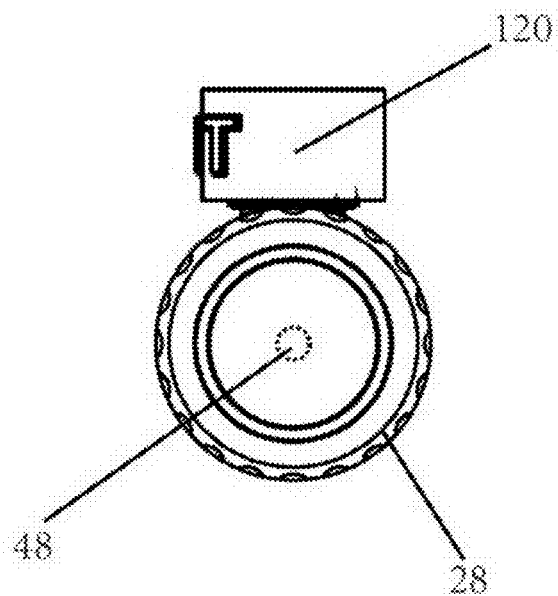
FIG. 5 is a bottom view of the mechanical smoking device in accordance with the invention showing an adapter in place.
Figure 9:
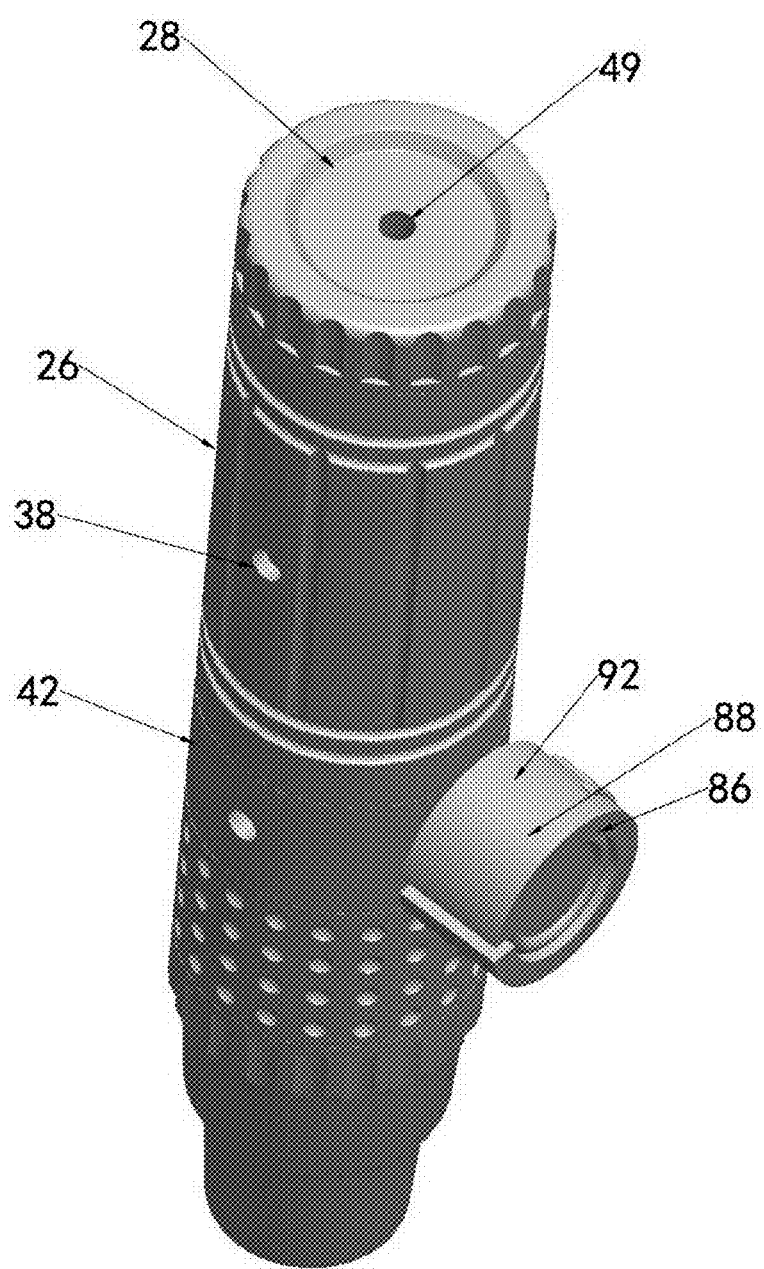
FIG. 9 is a bottom perspective of the mechanical smoking device in accordance with the invention.

In a preferred embodiment, since the battery 34 may be a lithium battery, it is desirable to include ventilation holes to avoid build of gas and heat that may adversely affect operation of the battery 34 and lead to its explosion. To this end, tube 26 includes one or more apertures 38 extending through the side wall, e.g., two as in the embodiment illustrated in FIGS. 1 and 4. Additionally, the closure element 28 may include an aperture 40 that extends entirely through it to provide a flow passage to the battery compartment 32 (see FIG. 9).

The housing 12 also includes an intermediate section having a hollow interior and that is engaged with the upper end of the tube 26, which in the illustrated embodiment is a substantially tubular intermediate ring section 42 engaged with the upper end of the tube 26. The engagement of the intermediate ring section 42 and the tube 26 may be a threaded engagement, e.g., threads are formed on an inner surface at the upper end of the tube 26 and corresponding threads on the outer surface of a lower rim of the intermediate ring section 42.

Intermediate ring section 42 houses or supports the heating system 16 and the manual activation system 18 and is a very important part of the smoking device 10.

Heating system 16 includes the electrode 36 and a coil assembly 44 including an electrically activated heating wire or coil 46. Electrode 36 has an elongate portion 48 and an enlarged bottom portion 50 with a lip 52 being defined therebetween (see FIG. 10). Electrode 36 is made of a conductive material, such as metal. The lip 52 of the electrode 36 allows the electrode 36 be inserted into an insulating ring 54 with the elongate portion 48 fitting into an axial passage 56 in the insulating ring 54 and the lip abutting against a lower surface of the insulating ring 54 to position the electrode 36. Insulating ring 54 also includes a flanged or disc-shaped lower portion 58 and a cylindrical shaft portion 60, in both of which the axial passage 56 is formed (see FIG. 10). The insulating ring 54 positions the electrode 36 so that the enlarged bottom portion 50 extends below the flanged lower portion 58 and can contact the battery 34 when it is present in the battery compartment 32, and part of the elongate portion 48 extends beyond the upper edge of the cylindrical portion 60 of the insulating ring 54.

Heating system 16 also includes a contact cylinder 62 that surrounds the cylindrical portion 60 of the insulating ring 54. Contact cylinder 62 is made of a conductive material, such as metal. A positioning ring 64 seats an upper flange 66 of the contact cylinder 62 in a secure position in the intermediate ring section 42 (see FIGS. 8 and 10).

Figure 10:
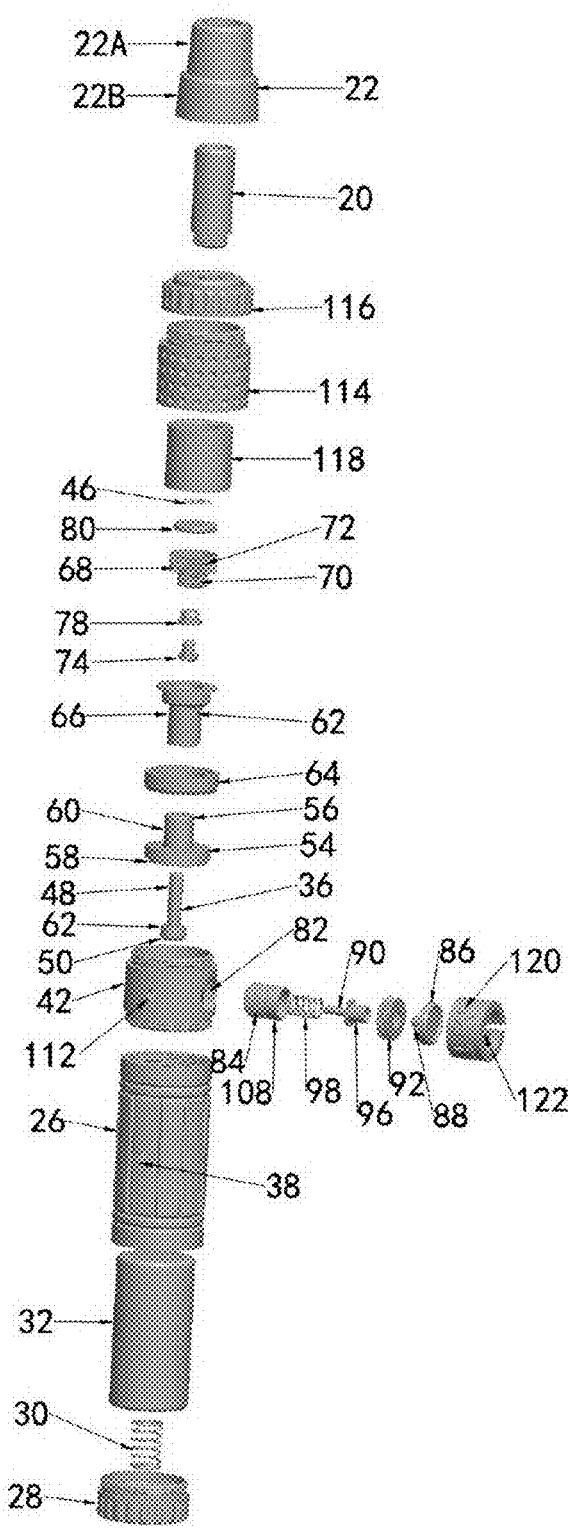
FIG. 10 is an exploded view of the mechanical smoking device in accordance with the invention.

Coil assembly 44 includes a coil housing 68 that engages with the contact cylinder 62 (see FIG. 10). The engagement of the coil housing 68 and the contact cylinder 62 may be a threaded engagement, e.g., threads are formed on an inner surface at the upper end of the contact cylinder 62 and corresponding threads on the outer surface of a lower rim of the coil housing 68. Coil housing 68 has a small diameter lower section 70 and a larger diameter upper section 72. A conductor element 74 extends below the lower section 70 and is configured to contact with exposed upper end of the electrode 36. Conductor element 74 has an axial passage.

Conductor element 74 is also in contact with the coil 46 exposed at the upper end of the coil assembly 44. An insulator ring 78 surrounds the conductor element 74 and is preferably made of a ceramic, or an electrically insulative or dielectric material to electrically insulate the coil housing 68 from the conductor element 74. Coil assembly 44 also includes a support disc 80 that supports the coil 46 and is housed in the larger diameter upper portion 72. Support disc 80 is also made of a ceramic, electrically insulative or dielectric material and includes apertures.

The manual activation system 18 is configured to engage with and pass through an opening 82 partly into the interior of the intermediate ring section 42. The manual activation system 18 may be a press button assembly as shown, see FIG. 10. The press button assembly includes a spring housing 84, a press button 86 having a projection 88 on an inward side, an actuating rod 90 that aligns with the projection 88, a spacer ring 92 that occupies space between the press button 86 and a flange 96 on the actuating rod 90 and a spring 98. The actuating rod 90 has a first portion 100 with a larger diameter than a second portion 102, with the flange 96 therebetween. The smaller diameter portion 102 is adapted to contact the contact cylinder 62. The larger diameter portion 104 is contacted by the projection 88 on the press button 86.

Press button 86 and the actuating rod 90 are both made of a conductive material, such as metal or a metal alloy such as brass. The actuating rod 90 may also be considered a thimble.

The spring 98 is retained at one end by the flange 96 and at the opposite end by a cavity 106 in the spring housing 84 (see FIG. 4), and is biased in a direction against the insertion of the press button 86. As such, force is required to press the press button 86 into the intermediate ring section 42 and upon release of this force, the spring 98 will expand and cause the press button 86 to be urged outward. Spring housing 84 may be a two-part construction including a upper housing part which is the spacer ring 92 and a lower housing part 108, both of which may made of a conductive material, such as metal or a metal alloy such as brass.

Spring housing 84 may engage with the opening 82, e.g., by means of a threaded engagement. To this end, the peripheral surface of the intermediate ring section 42 defining the opening 82 is provided with threads and the outer surface of the spring housing 84 is provided with corresponding threads. Other attachment techniques may be used.

In operation, a user presses the press button 86 inward against the bias of the spring 98 and must hold the press button 86 to create contact between the actuating rod 90 and the contact cylinder 62. Contact between the actuating rod 90 and the contact cylinder 62, while the user is holding the smoking device 10 in contact with the tube 26, causes completion of an electrical circuit that provides electrical power from the battery 34 to the heating system 16.

The manner in which this occurs may generally considered to be the conductance through the body of electricity to enable the 8-10 second contact of the actuating rod 90 and contact cylinder 62 to establish a current path to the contact cylinder 62 from a lower terminal of the battery 34 which in turn directs current through the coil housing 68 to one end of the coil 76 while the other path of current from the upper terminal of the battery 34 leads through the electrode 36 to the conductor element 74 connected to an opposite end of the coil 76. In this case, the coil 76 is connected in an electrical circuit and heats up. Control over the heating of the coil 76 is effected by controlling the pressing of the press button 86 against the spacer ring 92 of the spring housing 84. A user can thus hold the press button 86 in longer if they want a continued burning of material in the chamber 14.

The electrical circuit thus causes electrical energy from the battery 34 to flow to the coil assembly 44 and specifically, through the coil 46 therein. Properties and construction of the coil 46 to enable it to heat up to a specific temperature or temperature range when electricity is applied, i.e., when electrical current flows therethrough, to cause sufficient heating of the herb or other material are known to those skilled in the art.

Heat generated by the coil 46 may be dissipated through the apertures in the support disc 80, the axial passage in the conductor element 74, one or more apertures 110 in the contact cylinder 62, and one or more apertures 112 in the intermediate ring section 42 (e.g., two as in the illustrated embodiment).

Housing 12 also includes a connection ring 114 that houses the chamber 14. Connection ring 114 is engaged with the intermediate ring section 42 on one side and with a cover or retainer 116 on the other side. A tubular container 118 is arranged inside the connection ring 114 to actually define the chamber 14. The container 118 may be made of ceramic.

Retainer 116 is configured to removably connect to the mouthpiece 20. This removable connection may be by means of a threaded engagement, i.e., threads are formed on an inner surface defining an opening in an upper surface of the retainer 116 and corresponding threads are formed on the outer surface of a lower rim of the mouthpiece 20.

In a similar manner, engagement of the connection ring 114 and the intermediate ring section 42 may be a threaded engagement, e.g., threads are formed on an inner surface at the lower end of the connection ring 114 and corresponding threads are formed on the outer surface of an upper rim of the intermediate ring section 42. Engagement of the retainer 116 and the connection ring 114 may also be a threaded engagement, e.g., threads are formed on an inner surface at the lower end of the retainer 116 and corresponding threads are formed on the outer surface of an upper rim of the connection ring 114.

Retainer 116 includes a recessed circumferential lip that is configured to retain a lower flange of the cone 22. The cone 22 may thus be seated on the retainer 116. Retainer 116 optionally includes axially extending ridges which aid in rotation of the retainer 116, i.e., relative to the connection ring 114 when separation or attachment of the connection ring 114 to the retainer 116 is performed. Similarly, the connection ring 114 optionally includes dimples, the tube 26 optionally includes axially extending grooves and the closure element 28 optionally includes axially extending ridges, all of which may aid in separation or attachment of adjoining pats or serve purely ornamental purposes.

A protective ring 120 is provided to interpose a blocking element 122 between the press button 86 and the spring housing 90. This prevents the press button 86 from being pushed inward and thus inadvertent activation of the heating system 16. For use, the protective ring 120 is removed thereby allowing for inward pressing of the press button 86. Ring 120 may be made of silicone.

In preparation for use, a user separates the connection ring 114 from the retainer 116 or from the intermediate ring section 42 and places a quantity of herb into the chamber 14 defined by the container 118. If the connection ring 114 is separated from the retainer 116, the user would hold the smoking device upright and insert herbs into the open upper end of the container 118 against the coil 46. If the connection ring 114 is separated from the intermediate ring section 42, the user would invert the connection ring 114 and insert herbs into the open lower end of the container 118 against the retainer 116. The connection ring 114 is then re-engaged with the retainer 116 or the intermediate ring section 42 while preventing the herbs from falling out of the container 118.

The user then removes the protective ring 120 is present, and presses the press button 86 inward for about 8-10 seconds while holding the tube 26 of the smoking device 10, e.g., secured by the fingers and palm of the user's hand. This time may vary depending on the design of the smoking device.

Inward pressing of the press button 86 for a predetermined amount of time, say 8-10 seconds, causes the actuating rod 90 to contact the contact cylinder 62, and while the user is in physical contact with the tube 26, results in completion of an electrical circuit thereby provide electrical energy to the coil 46. The coil 46 is energized and heats up the herb that is in the chamber 14 in contact with or proximate the coil 46. The user then places their mouth over the mouthpiece 20, assuming the cone 22 has been removed, and inhales. Air from the chamber 14 passes through the apertures in the lower end of the mouthpiece 20 and into the user's mouth. When the cone 22 is present and placed into the inlet of a water pipe, the suction force generated by the water pipe causes air from the chamber 14 to pass through the apertures in the lower end of the mouthpiece 20 and into and through the mouthpiece 20 to the inlet of the water pipe.

Variations of the smoking device 10 are contemplated and considered to be part of the invention. In one embodiment, a pushing assembly is arranged in the chamber 14 to push the herb against the coil 46. The pushing assembly may include a perforated disc attached to one end of a spring with the other end of the spring attached to the retainer 116. By providing the pushing assembly, it can be better assured that herb will be in contact with the coil 46 and heat by the energization of the coil to enable inhalation of herb vapor-fused air.

Parts of the smoking device may be made of metal such as copper, and then possibly electroplated, or electroplated with copper, or made of metal alloys such as brass. These parts include, for example, one or more of the mouthpiece 20, the tube 26, the closure element 28, the electrode 36, the intermediate ring section 42, the contact cylinder 62, the coil housing 68, the spring housing 80, the press button 86, the actuating rod 90, the connection ring 114, and the retainer 116. The springs 30, 98 may be made of stainless steel.

Figure 11:
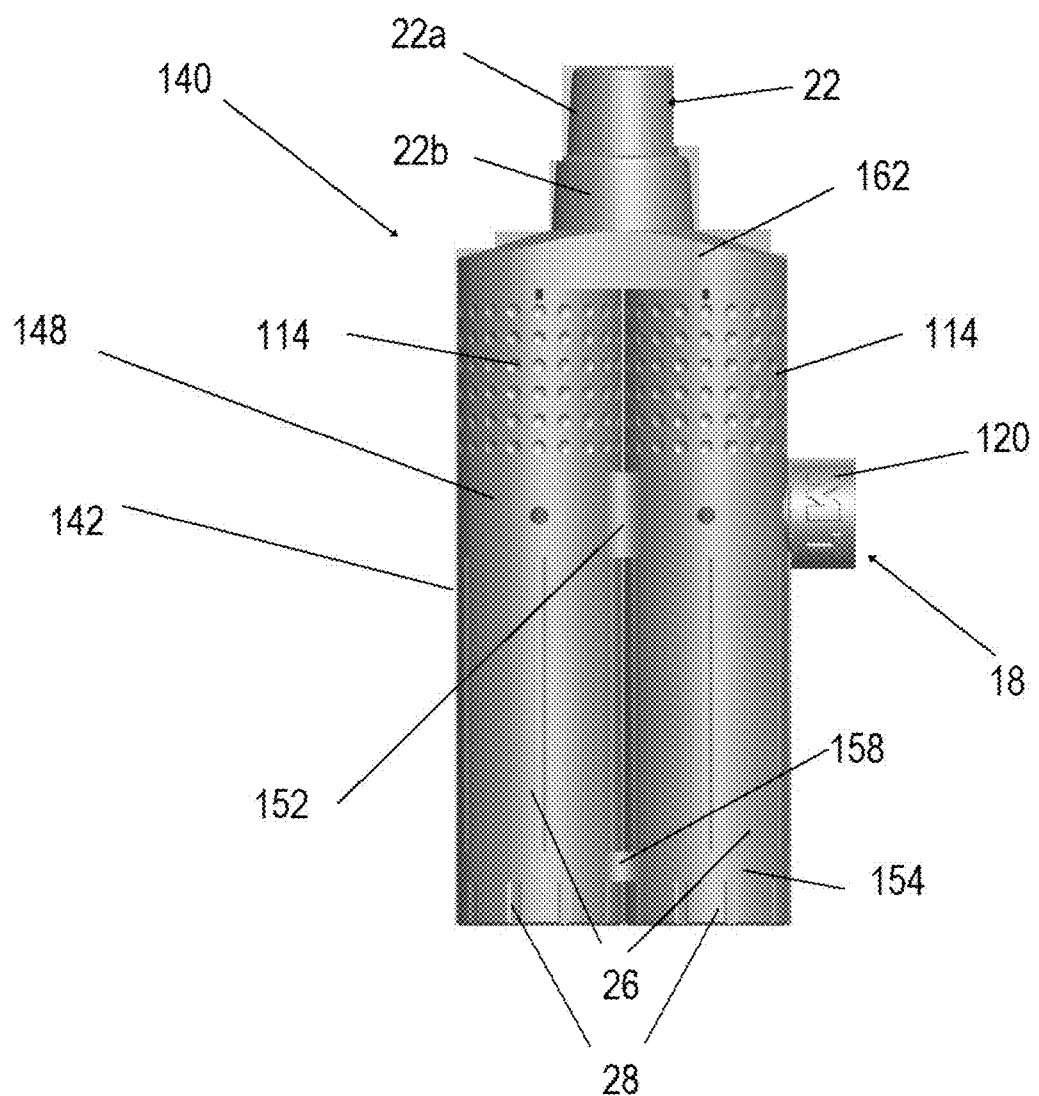
FIG. 11 is a front view of another embodiment of a mechanical smoking device in accordance with the invention.
Figure 12:
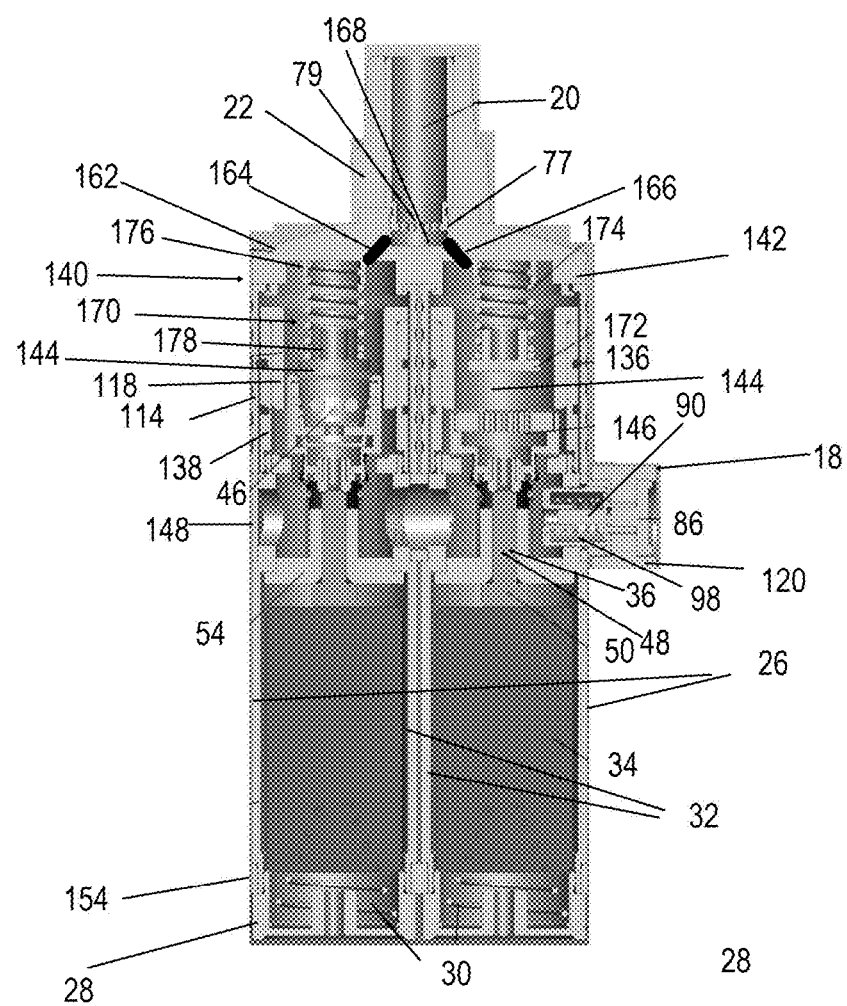
FIG. 12 is a cross-sectional view of the mechanical smoking device shown in FIG. 11.
Figure 13:
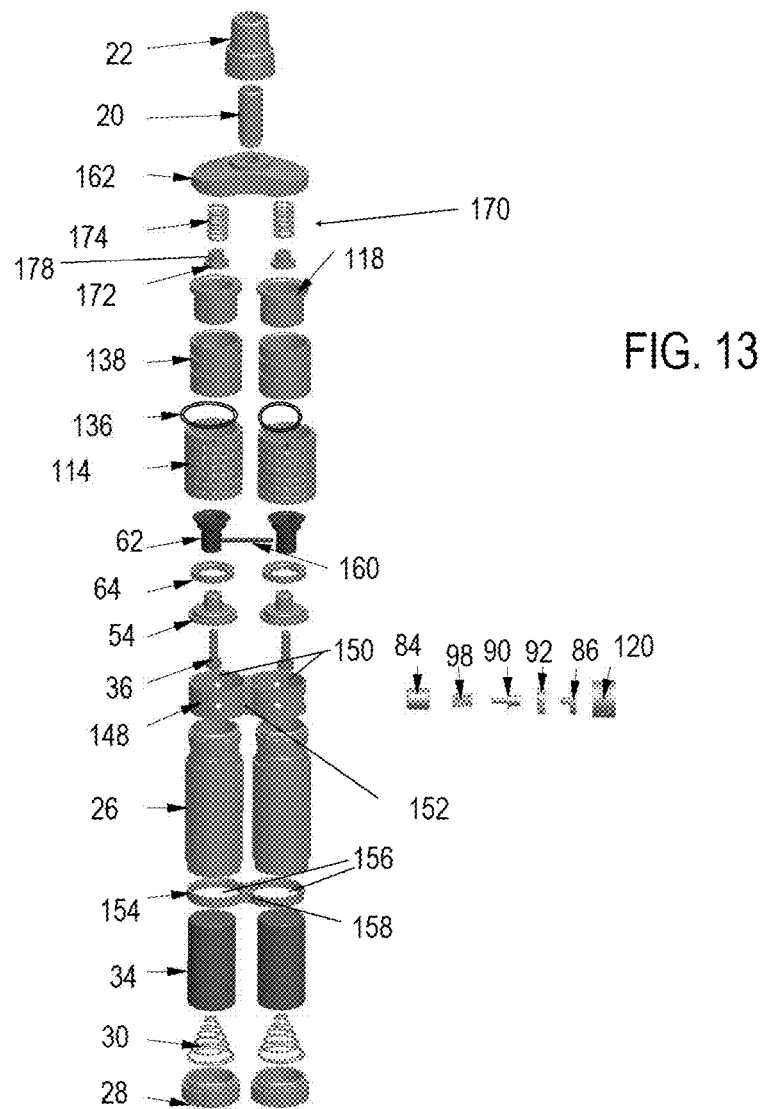
FIG. 13 is an exploded view of the mechanical smoking device shown in FIG. 11.

Referring now to FIGS. 11-13, another embodiment of a smoking device 140 in accordance with the invention is similar in its general construction and operation as smoking device 10 but includes two chambers into which different materials may be placed, but which lead to a common vapor outlet. As a result, this embodiment allows a user to selectively insert different materials into the two chambers and create a personalized, combined output vapor.

Smoking device 140 includes a number of the same components as smoking device 10 and only different components will be identified.

Smoking device 140 includes a housing 142 defining two separate chambers 144 into which a material sought to be heated and its vapor inhaled may be placed to be "smoked". Each chamber 144 is similar to chamber 14. Smoking device 140 also includes a common heating system 146 that heats the interior of the chambers 144 when activated by the manual activation system 18.

Housing 142 includes an intermediate ring section 148 defining two rings 150 connected together by a bridging portion 152, all of which may be made of metal. Intermediate ring section 148 houses or supports the manual activation system 18 (like intermediate ring section 42). A tube 26, closure element 28 and spring 30 are associated with each ring 150 and define battery compartments 32 each receivable of one or more batteries 34 (see FIG. 12). Each tube 26 and closure element 28, since they define a battery compartment 32, may be considered a battery housing. A lower ring section 154 defines two rings 156 connected by a bridging portion 158 and is situated near the location at which the closure elements 28 and the tubes 26 are connected together to provide for added stability to the smoking device 140. Lower ring section 154 may also be made of metal.

Heating system 146 is like heating system 16 except that two of each component are provided in two sets, each set of components being associated with a respective chamber 144 and battery compartment 32.

To enable the activation system 18 to activate the heating system 146, a conductive connector 160 connects the contact cylinders 62 that surround the cylindrical portions 60 of the insulating rings 54.

As a substitute for retainer 116 which connects the connection ring 114 to the mouthpiece 20, the housing 142 includes an upper cap 162 that includes two conduits, one conduit 164 leads from an area above the left chamber 144 and the other conduit 166 leads from an area above the right chamber 144, that combine into a single outflow conduit 168. Mouthpiece 20 is in flow communication with the single outflow conduit 168 (see FIG. 12). Multiple conduits 164, 166 may be provided from each chamber to the single outflow conduit 168 if so desired. The upper cap 162 may be configured to snap onto the connection rings 114, and is separated therefrom by applying force upward while holding the connection rings 114. Upper cap 162 may be made of a metal, and designed to conform in color and composition to the remainder of the housing 142 of the smoking device 140.

An additional feature of the smoking device 140 is the presence of a metallic inner tube or ring 138 between each ceramic ring 118 and the surrounding connection ring 114 (see FIG. 12). Sealing rings 136 are also provided to generate a seal between the connection rings 114 and the rings 138.

Operation of the smoking device 140 is similar to operation of smoking device 10. Prior to use, the user separates the upper cap 162 from the connection rings 114 and inserts whatever herbs or other material they want into the chambers 144. By selecting different materials, the user can customize a resultant vapor mixture. The upper cap 162 is then reengaged with the connection rings 114, and the user decides whether to use the smoking device 140 with only the mouthpiece 20 or with the cone 22, and appropriately configures the smoking device 140.

The user then presses the press button 86 inward against the bias of the spring 98 and hold the press button 86 to create contact between the actuating rod 90 and the contact cylinder 62 closest to the press button 86. Contact between the actuating rod 90 and the contact cylinder 62, while the user is holding the smoking device 140, causes completion of an electrical circuit that provides electrical power to the heating system 146. An exemplifying, non-limiting manner in which this occurs is described above. The circuit includes both contact cylinders 62 in view of the presence of the conductive connector 160 that connects the contact cylinders 62 together. The user controls the heating effect by the time that the press button 86 is depressed. Alternative constructions to complete a circuit based on depression of the press button 86 may also be used in the invention and would be readily determinable by those skilled in the art to which this invention pertains in view of the disclosure herein.

For the embodiment in FIG. 11-13, the heating system 146 is generally configured to allow contact between the actuating rod 90 and one of the contact cylinders 62 to cause heating of the coil heads 46 that form a surface defining both chambers 144. Other systems to allow a single depression of a button to effect heating by one or a plurality of heating elements of material in one or multiple chambers are also contemplated as being within the scope and spirit of the invention, with the parameters of the depression (e.g., time) being used to regulate the heating effect. Any mechanical, electrical and electro-mechanical system that converts user input into a heating effect may be applied in the invention, although the disclosed system is a preferred embodiment.

Also, although smoking device 140 includes two chambers 144 and two sets of components of the heating system for heating material in the chambers 144, a smoking device can be similarly designed with more than two chambers. A smoking device with any number of chambers, e.g., a plurality of chambers, is therefore within the scope and spirit of the invention.

FIG. 12 also shows a plunger system 170 that presses material in the chamber 144 against the coil 46. System 170 is designed to improve the heating of the material by providing a continual pressing force that presses the material against the coil 46 and dynamically adjusts to decreasing amounts of material during heating. The amount of material in the chamber 144 decreases as it is heated, or burned, and the system, 162 is designed to keep the material in contact with the coil 46 to ensure a better burning of the material.

Although the system 170 can have different forms, in the illustrated embodiment, the system 170 includes a board 172 at a lower end that may be made of ceramic or a similar non-conductive or combustible material (see FIG. 12). The board 172 is positioned substantially opposite the coil head 46. The board 172 is attached to a spring 174 that is retained or attached at its opposite end to the upper cap 162. A rim 176 may be formed on the underside of the cap 162 to retain each spring 174, i.e., be situated outward of the spring 174. Similarly, a cylindrical portion 178 may be formed on the board 172 to seat the board 172 on the spring 174. The use of a rim or cylindrical portion to seat an end of the spring 166 is at the discretion of the designer and each may be used, as well as other structure to retain an end of a spring). In use, the spring 174 biases the board 172 toward, and maybe against, the coil head 46 thereby pressing material between the board 172 and the coil head 46 against the coil head 46 causing it to be better heated by the coil head 46.

System 170 may be used in all of the other embodiments disclosed herein. Thus, for example, in the smoking device 10, the retainer 116 may be provided with a rim or cylindrical portion to secure an end of the spring. With the other end of the spring secured to a board that is able to plunge into the chamber 14 to press the material in the chamber 14 against the coil head during use of the smoking device 10.

The use of one or more batteries as described above to power the heating system 16, 146 is an example of an electrical supply unit that is needed to enable heating of the material in the chambers 14, 144. Alternative electrical supply units may be used in smoking devices 10, 140, for example, a single battery pack for multiple chambers in smoking device 140. Construction of a smoking device with alternative electrical supply units to that disclosed above is contemplated by the inventor. The manner in which alternative constructions may be made and used is within the purview of those skilled in the art to which this invention pertains and to those skilled in the art of electric-powered handheld appliances.

A preferred use of the smoking devices 10, 140 is for the heating of herbs and other natural materials that generate desired vapors upon being heated.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

The invention claimed is:

1. A device for heating material for use in inhalation, comprising:
   a housing defining two battery compartments and two separate material chambers each adapted to receive material, each of said battery compartments being adapted to receive at least one battery;
   a selectively activated heating system that heats material in each of said chambers when the material is in contact with part of said heating system, said heating system comprising two conductive electrodes each having a portion extending into a respective one of said battery compartments and adapted to be electrically coupled to the at least one battery when present in the respective one of said battery compartments;
   an activation system that activates said heating system; and
   an outlet portion comprising a mouthpiece having an interior in flow communication with each of said chambers, and an adapter configured to fit over said mouthpiece, said outlet portion having a first configuration when said adapter is not over said mouthpiece and a second configuration when said adapter is over said mouthpiece and provides an outer circumference for said outlet portion that is larger than the outer circumference provided when said adapter is not over said mouthpiece,
   said housing comprising:
      an intermediate ring section defining two rings and a bridging portion connecting said two rings together; and
      two battery housings each connected to said intermediate ring section and defining a respective one of said battery compartments,
   whereby a user can place their mouth over said mouthpiece and directly inhale material being heated in said chambers or connect an inlet of an inhaling appliance to said adapter when said adapter is fit over said mouthpiece.

2. The device of claim 1, wherein each of said battery housings comprises:
   a tube having an upper end engaged with a respective one of said rings of said intermediate ring section and an opposite lower end;
   a closure element removably engaging with the lower end of said tube to selectively close the lower end of said tube; and
   a spring attached to said closure element and that urges the at least one battery when present in said battery housing against the portion of said electrode extending into the respective one of said battery compartments.

3. The device of claim 2, wherein said housing further includes a lower ring section defining two rings and a bridging portion connecting said two rings of said lower ring section together, said lower ring section being situated near a location at which said closure elements and said tubes engage with one another.

4. The device of claim 1, wherein said heating system and said activation system are each partly housed in or supported by said intermediate ring section.

5. The device of claim 1, wherein said heating system further comprises a respective set of components associated with each of said chambers, each of said sets of components comprising a coil assembly including a coil housing, an electrically activated coil arranged on said coil housing and a conductor element extending below said coil housing and connected to said coil, and a contact cylinder surrounding a portion of a respective one of said electrodes and electrically insulated therefrom, said contact cylinder engaging with said coil housing, the respective one of said electrodes contacting said conductor element of said coil assembly, said heating system further comprising a conductive connector that connects said contact cylinders together.

6. The device of claim 5, wherein said activation system comprises a spring housing extending through an opening in a side wall of said housing, a conductive press button, a conductive actuating rod movable upon inward movement of said press button, and a spring arranged at least partly in said spring housing and that biases said press button to a position in which said activation system is not activating said heating system, said actuating rod contacting one of said contact cylinders when said press button is moved inward to cause completion of an electrical circuit that provides electrical power to said heating system from the at least one battery when present in a respective one of said battery compartments and said coil to heat up.

7. The device of claim 5, further comprising a support disc that supports said coil in said coil housing.

8. The device of claim 1, wherein said outlet portion comprises an upper cap that includes a first conduit leading from an area above a first one of said two chambers, a second conduit leading from an area above a second one of said two chambers, and a single outflow conduit communicating with said first and second chambers and in flow communication with said mouthpiece.

9. The device of claim 1, further comprising a plunger system that presses material in a respective one of said chambers against said part of said heating system when the material is present in the respective one of said chambers.

10. The device of claim 9, wherein said plunger system comprises a spring retained at one end on said housing and a board attached at an opposite end of said spring and that is urged by said spring toward said part of said heating system.

11. A device for heating material for use in inhalation, comprising:
   a housing defining two material chambers each adapted to receive material and two battery compartments each receivable of at least one battery and associated with a respective one of said chambers, said housing comprising:
      an intermediate ring section defining two rings and a bridging portion connecting said two rings together; and
      two battery housings each connected to said intermediate ring section and defining a respective one of said battery compartments;
   a heating system that heats material in each of said chambers;
   an activation system that activates said heating system; and
   an outlet portion comprising:
      an upper cap that includes a first conduit leading from an area above a first one of said chambers, a second conduit leading from an area above a second one of said chambers, and a single outflow conduit communicating with said first and second chambers, and
      a mouthpiece in flow communication with said single outflow conduit.

12. The device of claim 11, wherein said outlet portion further comprises an adapter configured to fit over said mouthpiece, said outlet portion having a first configuration when said adapter is not over said mouthpiece and a second configuration when said adapter is over said mouthpiece and provides an outer circumference for said outlet portion that is larger than the outer circumference provided when said adapter is not over said mouthpiece.

13. The device of claim 11, wherein said heating system comprises a plurality of conductive electrodes each having a portion extending into a respective one of said battery compartments and adapted to be electrically coupled to the at least one battery when present in the respective one of said battery compartments.

14. The device of claim 11, wherein each of said battery housings comprises:
   a tube having an upper end engaged with a respective one of said rings of said intermediate ring section and an opposite lower end;
   a closure element removably engaging with a lower end of said tube to selectively close the lower end of said tube; and
   a spring attached to said closure element and that urges the at least one battery when present in said battery housing against the portion of said electrode extending into the respective one of said battery compartments.

15. The device of claim 14, wherein said housing further includes a lower ring section defining two rings and a bridging portion connecting said two rings of said lower ring section together, said lower ring section being situated near a location at which said closure elements and said tubes engage one another.

16. The device of claim 11, wherein said heating system further comprises a respective set of components associated with each of said chambers, each of said sets of components comprising a coil assembly including a coil housing, an electrically activated coil arranged on said coil housing and a conductor element extending below said coil housing and connected to said coil, and a contact cylinder surrounding a portion of said electrode and electrically insulated therefrom, said contact cylinder engaging with said coil housing, said electrode contacting said conductor element of said coil assembly, said heating system further comprising a conductive connector that connects said contact cylinders together.

17. The device of claim 16, wherein said activation system comprises a spring housing extending through an opening in a side wall of said housing, a conductive press button, a conductive actuating rod movable upon inward movement of said press button, and a spring arranged at least partly in said spring housing and that biases said press button to a position in which said activation system is not activating said heating system, said actuating rod contacting one of said contact cylinders when said press button is moved inward to cause completion of an electrical circuit that provides electrical power to said heating system from the at least one battery when present in one of said battery compartments and said coil to heat up.

18. The device of claim 11, further comprising a plunger system that presses material in one of said chambers against a part of said heating system when the material is present in said one of said chambers, said plunger system comprising a spring retained at one end on said housing and a board attached at an opposite end of said spring and that is urged by said spring toward said part of said heating system.

19. A device for heating material for use in inhalation, comprising:
   a housing defining a battery compartment adapted to receive at least one battery and a material chamber adapted to receive material;
   a selectively activated heating system that heats material in said chamber when the material is present in said chamber and in contact with part of said heating system, said heating system comprising a conductive electrode having a portion extending into said battery compartment and adapted to be electrically coupled to the at least one battery when present in said battery compartment;
   an activation system that activates said heating system;
   an outlet portion comprising a mouthpiece having an interior in flow communication with said chamber, and an adapter configured to fit over said mouthpiece, said outlet portion having a first configuration when said adapter is not over said mouthpiece and a second configuration when said adapter is over said mouthpiece and provides an outer circumference for said outlet portion that is larger than the outer circumference provided when said adapter is not over said mouthpiece; and
   a plunger system that presses the material in said chamber against said part of said heating system when the material is present in said chamber,
   whereby a user can place their mouth over said mouthpiece and inhale material being heated in said chamber or connect an inlet of an inhaling appliance to said adapter when said adapter is fit over said mouthpiece.

20. The device of claim 19, wherein said plunger system comprises a spring retained at one end on said housing and a board attached at an opposite end of said spring and that is urged by said spring toward said part of said heating system.

21. A device for heating material for use in inhalation, comprising:
   a housing defining two material chambers each adapted to receive material;
   a heating system that heats material in said chambers;
   an activation system that activates said heating system;
   a plunger system that presses material in a respective one of said chambers against a part of said heating system when the material is present in said chamber, said plunger system comprising a spring retained at one end on said housing and a board attached at an opposite end of said spring and that is urged by said spring toward said part of said heating system; and
   an outlet portion comprising:
   an upper cap that includes a first conduit leading from an area above a first one of said chambers, a second conduit leading from an area above a second one of said chambers, and a single outflow conduit communicating with said first and second chambers, and
   a mouthpiece in flow communication with said single outflow conduit.

* * * * *